US008906837B2

(12) United States Patent
Allef et al.

(10) Patent No.: US 8,906,837 B2
(45) Date of Patent: Dec. 9, 2014

(54) SKIN AND HAND CLEANING MEANS CONTAINING SUPER-ABSORBING PARTICLES

(75) Inventors: Petra Allef, Essen (DE); Thomas Mangen, Duesseldorf (DE); Laurent Wattebled, Duesseldorf (DE); Christian Schmidt, Krefeld (DE); Frank Loeker, Krefeld (DE)

(73) Assignee: DEB IP Limited, Denby (GB)

( * ) Notice: Subject to any disclaimer, the term of this patent is extended or adjusted under 35 U.S.C. 154(b) by 17 days.

(21) Appl. No.: 14/001,512

(22) PCT Filed: Jan. 30, 2012

(86) PCT No.: PCT/EP2012/051414
§ 371 (c)(1),
(2), (4) Date: Aug. 26, 2013

(87) PCT Pub. No.: WO2012/116864
PCT Pub. Date: Sep. 7, 2012

(65) Prior Publication Data
US 2013/0338052 A1 Dec. 19, 2013

(30) Foreign Application Priority Data
Feb. 28, 2011 (DE) .......................... 10 2011 004 815

(51) Int. Cl.
| C11D 3/37 | (2006.01) |
| A61K 8/02 | (2006.01) |
| A61K 8/73 | (2006.01) |
| A61K 8/46 | (2006.01) |
| C11D 3/14 | (2006.01) |
| A61K 8/39 | (2006.01) |
| A61Q 19/10 | (2006.01) |
| C11D 17/00 | (2006.01) |
| C11D 3/22 | (2006.01) |
| A61K 8/81 | (2006.01) |
| A61Q 17/00 | (2006.01) |

(52) U.S. Cl.
CPC .............. *A61K 8/8147* (2013.01); *A61K 8/0241* (2013.01); *A61K 8/731* (2013.01); *A61K 2800/546* (2013.01); *A61K 8/463* (2013.01); *C11D 3/37* (2013.01); *A61K 2800/412* (2013.01); *C11D 3/14* (2013.01); *A61K 8/39* (2013.01); *A61Q 19/10* (2013.01); *C11D 17/0013* (2013.01); *C11D 3/222* (2013.01); *A61Q 17/005* (2013.01); *A61K 8/732* (2013.01); *A61K 2800/28* (2013.01)
USPC .......... 510/138; 510/130; 510/132; 510/137; 510/139; 510/398; 510/399; 510/434

(58) Field of Classification Search
USPC ......... 510/130, 132, 138, 137, 139, 398, 399, 510/434
See application file for complete search history.

(56) References Cited

U.S. PATENT DOCUMENTS

| 5,658,577 A | 8/1997 | Fowler et al. |
| 5,723,112 A | 3/1998 | Bowser et al. |
| 6,342,473 B1 | 1/2002 | Kott et al. |
| 7,163,916 B2 | 1/2007 | Allef et al. |
| 7,173,086 B2 | 2/2007 | Smith et al. |
| 7,297,675 B2 | 11/2007 | Allef et al. |
| 7,777,093 B2 | 8/2010 | Smith et al. |
| 7,842,386 B2 | 11/2010 | Loeker et al. |
| 7,847,123 B2 | 12/2010 | Wenk et al. |
| 7,851,511 B2 | 12/2010 | Allef et al. |
| 7,906,664 B2 | 3/2011 | Allef et al. |
| 7,910,119 B2 | 3/2011 | Allef et al. |
| 8,138,372 B2 | 3/2012 | Herrwerth et al. |
| 8,211,841 B2 | 7/2012 | Allef et al. |
| 8,252,847 B2 | 8/2012 | Veeger et al. |
| 8,283,299 B2 | 10/2012 | Allef et al. |
| 8,288,002 B2 | 10/2012 | Loeker et al. |
| 8,466,097 B2 | 6/2013 | Allef et al. |
| 8,491,920 B2 | 7/2013 | Veeger et al. |
| 8,518,541 B2 | 8/2013 | Loeker et al. |
| 2003/0012760 A1* | 1/2003 | Jehn-Rendu et al. ...... 424/70.15 |
| 2003/0108534 A1 | 6/2003 | Chokri et al. |
| 2003/0171230 A1 | 9/2003 | Shana'a et al. |
| 2006/0198859 A1 | 9/2006 | Allef et al. |
| 2007/0092470 A1 | 4/2007 | Allef et al. |

(Continued)

FOREIGN PATENT DOCUMENTS

| DE | 102 33 834 A1 | 2/2004 |
| EP | 0 392 248 A1 | 10/1990 |

(Continued)

OTHER PUBLICATIONS

International Search Report and Written Opinion issued Mar. 3, 2014 in PCT/EP2012/051414 with English Translation of Category of Cited Documents.
Examination Report issued Nov. 9, 2011 in German Patent Application No. 10 2011 004 815.4.
J. Falbe,"Katalysatoren, Tenside und Mineralöladditive,(catalysts, surfactants and mineral oil additives)", Thieme Verlag, Stuttgart 1978, pp. 123-217.

(Continued)

Primary Examiner — Charles Boyer
(74) Attorney, Agent, or Firm — Oblon, Spivak, McClelland, Maier & Neustadt, L.L.P.

(57) ABSTRACT

The invention relates to compositions containing at least 10 wt.-% of water in relation to the total composition, if required, one or more additional solvents, optionally one or more emollients, if necessary, one of more emulsifiers, one or more surfactants which are different from the emulsifiers. The compositions being characterized such that they contain 0.01-30 wt.-% of super absorbing particles in relation to the total composition, and to the use thereof as skin and hand cleaning means.

14 Claims, No Drawings

(56) References Cited

U.S. PATENT DOCUMENTS

| | | |
|---|---|---|
| 2007/0134304 A1* | 6/2007 | Aubrun-Sonneville et al. .......................... 424/443 |
| 2008/0009616 A1 | 1/2008 | Frank et al. |
| 2008/0153730 A1* | 6/2008 | Tsaur et al. .................. 510/159 |
| 2009/0013040 A1 | 1/2009 | Sawada |
| 2009/0298902 A1 | 12/2009 | Taranta et al. |
| 2010/0028295 A1 | 2/2010 | Taranta et al. |
| 2010/0075844 A1 | 3/2010 | Loeker et al. |
| 2010/0249011 A1 | 9/2010 | Moore et al. |
| 2010/0279860 A1 | 11/2010 | Smith et al. |
| 2011/0009272 A1 | 1/2011 | Wattebled et al. |
| 2011/0206623 A1 | 8/2011 | Wenk et al. |
| 2012/0001122 A1 | 1/2012 | Wattebled et al. |
| 2012/0101060 A1 | 4/2012 | Thoerner et al. |
| 2012/0302445 A1 | 11/2012 | Rudolph et al. |
| 2012/0308492 A1 | 12/2012 | Allef et al. |

FOREIGN PATENT DOCUMENTS

| | | |
|---|---|---|
| EP | 1 210 059 A | 6/2002 |
| WO | WO 2004/013269 A1 | 2/2004 |
| WO | WO 2010/110898 A1 | 9/2010 |

OTHER PUBLICATIONS

J. Falbe, "Surfactants in Consumer Products", Springer Verlag, Berlin, 1987, pp. 54-124.

* cited by examiner

SKIN AND HAND CLEANING MEANS CONTAINING SUPER-ABSORBING PARTICLES

The present invention relates to compositions comprising solvents, in particular water, optionally one or more emollients, optionally one or more emulsifiers, one or more surfactants which are different from the emulsifiers, and from 0.01 to 30% by weight, based on the total composition, of superabsorbent particles, and use of these compositions as skin and hand cleansers.

To remove stubborn soilings from skin and hands which are caused by paints, greases, oils, lubricants, metal dusts, graphite, soot and the like, numerous products have been developed, in particular so-called heavy-duty cleansers. These products, which are used extensively in industry, generally have abrasives, which are intended to assist the removal of the stubborn soilings.

The more often such products are applied to the skin in the industrial sector (up to 6 times and more often per day) the more considerable the disadvantageous effects of the abrasives, surfactants or surfactant mixtures and in particular also solvents, such as, for example, aliphatic hydrocarbons, terpenes, carboxylic acid esters of the type dimethyl adipate, dimethyl glutarate, dimethyl succinate (DBE) and di-n-butyl adipate or diisopropyl adipate, which have been described in DE 4335933 A1, present in these heavy-duty hand cleansers come to the fore, namely the degreasing and drying out of the skin through the destruction of the hydro-lipid mantle of the skin. This can then lead to increased absorption of toxic or allergenic substances or to attack by microorganisms and, consequently, it may lead to toxic or allergenic skin reactions.

One difficulty when providing such heavy-duty hand cleansers is therefore to find the ideal balance between cleaning power and impairment of the skin.

To avoid the aforementioned skin problems, a large number of formulations for heavy-duty hand cleansers have been proposed. Thus, for example, WO 99/06021 describes formulations which have a water content of from 75 to 99% by weight, up to 25% by weight of a fatty acid ester or mixtures of such esters, and at least one surfactant. Compared with the aforementioned products comprising organic solvents, such formulations constitute a significant improvement, particularly from a toxicological point of view. Nevertheless, the improved skin compatibility and also the improved protection against the drying out of the skin was accompanied by a loss in cleaning effect compared to solvent-containing heavy-duty hand cleansers.

DE 19748921 A1 relates to hydrous, liquid, pasty or creamy hand cleansers, in particular heavy-duty hand cleansers with 1 to 30% by weight of an abrasive which have a content of from 10 to 30% by weight of at least one vegetable oil, selected from the group of triglycerides, saturated and/or unsaturated fatty acids, from 10 to 30% by weight of at least one surfactant from the group fatty alcohol ethoxylates, fatty alcohol ether sulphates and/or castor oil sulphonates, and also 10 to 65% by weight of water, in each case based on the composition of the cleansers. The heavy-duty hand cleansers described therein are said to be highly skin compatible and only have slight drying-out of the skin even upon repeated daily use.

EP 1152051 A2 discloses skin-mild handwashing pastes without abrasives, where fatty acid alkyl esters are used in combination with emulsifiers, preferably fatty alcohol ethoxylates. Although in the examples an excellent skin compatibility and cleaning power is attested to the formulations, the suitability of these mild handwashing pastes as means for removing stubborn soilings has not been indicated.

DE 19916036 A1 describes handwashing pastes comprising anionic surfactants, abrasive bodies and partial glycerides, in particular oleic acid monoglycerides, and also the use of such partial glycerides for improving the skin feel. Although the handwashing pastes described in this laid-open specification are said to lead to a subjective improvement in skin feel, no experimental data for this are given which could demonstrate such an improvement in the condition of the skin.

WO 2008/138708 offers mild skin and hand cleansers which ensure a very good cleaning effect even in the case of stubborn skin soilings, coupled with very good skin compatibility and which have a content of at least 0.1% by weight of at least one hydrophilic emollient with an HLB value of $\geq 10$, where polyol esters are particularly preferred as hydrophilic emollients. In the cleanser specified here too, abrasives, in particular natural kernel flours, are used in order to increase the cleaning power.

In summary, it can be established that, in the prior art, in order to increase the cleaning power of hand or skin cleansers, either special, particularly efficient surfactants, or else abrasives (abrasive bodies) are used. However, both components often lead to mechanical or chemical destruction of the skin.

WO 2009/144139 describes anhydrous or low-water skin and hand cleansers, especially for removing extreme skin soilings, which can have, as abrasives, water-swellable polymers based on monoethylenically unsaturated carboxyl-group-carrying monomers.

WO 01/64179 (DE 10195737 T5) describes skin gumming agents and cosmetic formulations, in particular skin peels or products which allow dead skin cells on the face or body to be removed. Crosslinked polymers from the family of superabsorbents are used as peels. By using these peels, the aim is to reduce the reddening of the skin which arises when using customary scouring agents. Aqueous solutions, liquid soap, gel creams and emulsions are described as formulations. A particular suitability of the formulations as skin or hand cleansers to combat stubborn dirt (heavy-duty hand cleansers) is not described.

There was therefore still a need to provide skin and/or hand cleansers which do not have one or more of the aforementioned disadvantages and which in particular have a high cleaning power coupled with the greatest possible skin compatibility.

Surprisingly, it has been found that by using superabsorbent particles in mild cleansing compositions, the cleaning power of such compositions can be increased without resulting in the mechanical impairments of the skin known from using abrasives.

The present invention therefore provides compositions comprising 10% by weight or more, based on the total composition, of water, and also optionally further solvents, optionally one or more emollients, optionally one or more emulsifiers, one or more surfactants which are different from the emulsifiers, which are characterized in that they have from 0.01 to 30% by weight, based on the total composition, of superabsorbent particles, and their use as skin and hand cleansers.

The compositions according to the invention have the advantage that they have a good hand and skin cleaning effect, particularly towards stubborn soilings such as, for example, greases, soots, dyes, paints and oils, and at the same time have no, or only a minimal, mechanical stressing of the skin.

Through the preferred use of mild surfactants or surfactant mixtures, moreover, the chemical stressing of the skin/hands is minimized.

Moreover, the compositions according to the invention have the advantage that they can be prepared free from organic solvents and the composition does not leave behind an oily impression and/or an oily skin feel for the user.

The present invention is described below by way of example without any intention of limiting the invention to these exemplary embodiments. Where ranges, general formulae or compound classes are stated below, then these are intended to encompass not only the corresponding ranges or groups of compounds that are explicitly mentioned, but also all part ranges and part groups of compounds which can be obtained by removing individual values (ranges) or compounds. Wherever documents are cited in the course of the present description, then their content, in particular the aspect specified in the citation, should be deemed, in its entirety, as belonging to the disclosure content of the present invention. Unless stated otherwise, all % data below are data in % by mass, and all average data are number-average data.

The compositions according to the invention comprising 10% by weight or more, based on the total composition, of water and optionally further solvents, optionally one or more emollients, optionally one or more emulsifiers, one or more surfactants which are different from the emulsifiers, are characterized in that they have from 0.01 to 30% by weight, preferably 1 to 30% by weight, preferably from 1 to 10% by weight and particularly preferably from 2 to 8% by weight, based on the total composition, of superabsorbent particles.

The compositions according to the invention preferably have a viscosity at 20° C. of greater than 2000 mPas, preferably from 10 000 mPas to 80 000 mPas, particularly preferably from 20 000 to 40 000 mPas and very particularly preferably from 20 000 to 30 000 mPas. This distinguishes compositions according to the invention from liquid soaps, which usually have a viscosity of less than or equal to 2000 mPas. Preferably, the composition according to the invention is not a product commonly termed liquid soap. The determination of the viscosity at 20° C. can take place e.g. using a Brookfield RVT rotary viscometer at 20 rpm, using a spindle suitable for the viscosity range, preferably spindle 7. Preferred adjustment of the viscosity to the specified ranges means that they can be dispensed easily from wall-mounted dispensers.

a) Superabsorbent Particles

Within the context of the present invention, superabsorbent particles are understood as meaning those particles which are water-insoluble and can absorb at least 10 times, preferably at least 100 times and preferably 100 to 1500 times, their own weight in water (distilled water). The water absorption capacity of particles is preferably determined in accordance with EDANA Recommended Test Methods (ERT) 440.2-02 ("Free swell capacity", EUROPEAN DISPOSABLES AND NONWOVENS ASSOCIATION, Avenue Eugéne Plasky, 157-1030 Brussels—Belgium).

A further option for characterizing superabsorbent particles is the retention capacity of absorbed water. This is determined in accordance with ERT 441.2-02 ("Centrifuge retention capacity", CRC) and should preferably be from 1 to 80 g/g, preferably from 5 to 60 g/g, particularly preferably from 10 to 50 g/g.

Particles which can be used are in principle all superabsorbent particles, irrespective of their mode of production, thus e.g. those which are obtainable by bulk polymerization, solution polymerization or emulsion polymerization. Preferably, the composition according to the invention has superabsorbent particles which have a particle size, determined in accordance with ERT 420.2-02 of from 0.01 to 2 mm, preferably from 0.02 to 1 mm and particularly preferably from 0.05 to 0.5 mm. Very particularly preferably, the composition according to the invention has particles which have a particle size of less than or equal to 0.2 mm or greater than or equal to 0.65 mm, preferably a particle size of from 0.01 to 0.2 mm or from 0.65 to 2 mm, preferably a particle size of from 0.02 to 0.15 mm or from 0.7 to 1.5 mm. The particle size can be determined using the instrument PartAn 2001 F/L from Anatec AS, Porsgrunn, Norway and the associated PartAn software. Particular preference is given to using particle fractions which exclusively have particles which have a particle size within the limits stated above.

A selection of particles with preferred particle size and/or suitable or preferred particle size fractions can be obtained by methods known to the person skilled in the art, such as e.g. sieving, sifting or classification. If necessary, the particle size can be reduced by means of suitable measures, such as e.g. by grinding, with grinding preferably being dispensed with following any surface crosslinking.

The superabsorbent particles can have the materials known per se from the prior art as superabsorbent material. Preferably, as superabsorbent material, the particles have a homopolymer of acrylic acid or a copolymer of at least acrylic acid and alkali metal acrylate, in particular sodium acrylate. These homopolymers or copolymers can be crosslinked in a manner known per se and/or be surface-aftercrosslinked and/or surface-treated or further treated in another way.

The production of superabsorbent materials and a selection of suitable superabsorbent materials can be found in e.g. U.S. Pat. No. 3,669,103, which describes weakly crosslinked polymers, such as poly-N-vinylpyrrolidone, polyvinyltoluene sulphonate, polysulphoethyl acrylate, poly-2-hydroxyethyl acrylate, polyvinylmethyloxazolidinone, hydrolysed polyacrylamide, polyacrylic acid, copolymers of acrylamide and acrylic acid and alkali metal salts of polymers which contain sulphonate or carboxy groups, in particular partially hydrolysed weakly crosslinked polyacrylamide, or FR 2559158 which describes crosslinked polymers of acrylic acid or methacrylic acid, refined crosslinked copolymers of the polysaccharide/acrylic acid or methacrylic acid type, crosslinked terpolymers of the acrylic acid or methacrylic acid/acrylamide/sulphurated acrylamide type and their alkaline earth metal or alkali metal salts.

Superabsorbent materials/particles which can be used are preferably also those which are based completely or partly on polysaccharides and/or natural and/or renewable raw materials. Such materials are described e.g. in DE 10125599A1.

As superabsorbent materials/particles, preference is given to using those as are described e.g. in DE 10334286, DE 102006037983, DE 4021847, DE 10334286, DE 102007053619, DE 102007024080, DE 102007045724, WO 94/20547/EP 0688340, WO 93/21237/EP 0 636 149, WO 2003/022 896/EP 1 427 762 and/or WO 98/49221/EP 0979250.

As superabsorbent materials/particles, preference is given to those as are described in DE 102006037983 A1, in particular as powders C, C3, A, A1, A2, in US 2008234420 A1, in particular as preproduct B and product of Example 10, DE 10125599A1, in particular in Example 3, DE 102004030182, in particular in Example 1, and DE 102005013893A1, in particular in Example 1.

Particularly preferred superabsorbent particles are in particular those which are available under the trade names FAVOR® from Evonik Stockhausen GmbH, AQUALIC® CA/CS from Nippon Shokubai or HYSORB® from BASF SE. In some circumstances, it may be necessary to obtain a suitable or preferred particle size fraction from the specified products by methods known to the person skilled in the art, such as e.g. sieving, sifting or classification.

For sensory reasons, it has proven to be advantageous if the superabsorbent materials/particles used are those which are preferably highly crosslinked and particularly preferably highly crosslinked and postcrosslinked polymers and particularly preferably highly crosslinked and surface-postcrosslinked polymers which preferably have a lower tendency to swell.

It has been found that compositions in whose preparation superabsorbent particles are used which, following their production, in particular after crosslinking (crosslinking, highcrosslinking and/or post-crosslinking), have been ground to achieve a desired particle size, have a poorer cleaning power than those for which grinding is omitted. It is therefore particularly preferred to use those superabsorbent particles which have not been subjected to a grinding process.

b) Solvents

The fraction of solvents (water and optionally further solvents) in the composition according to the invention is preferably 30 to 90% by weight, preferably 40 to 80 and particularly preferably 45 to 75% by weight. Solvents which may be present in the composition according to the invention are all solvents that are suitable for skin and hand cleansers. As optional further solvent, an alcohol, in particular monoalcohols having 1 to 4, preferably 2 to 4, carbon atoms and/or a methyl ester or ethyl ester of a mono- or dicarboxylic acid is preferably present in the composition. Preferably, the solvent present in the composition according to the invention is exclusively water. The fraction of water in the composition according to the invention is particularly preferably 30 to 90% by weight, preferably 40 to 80 and particularly preferably 45 to 75% by weight. The fraction of water/solvent in the composition is the sum of "free" water/solvent and also water/solvent absorbed in the superabsorbent particles.

c) Emollients

It may be advantageous if the composition according to the invention has one or more emollients. The content of emollients, based on the total composition, is preferably from 0.05 to 10% by weight, preferably 0.1 to 5 and particularly preferably 0.3 to 3% by weight.

As emollient, it is possible to use all emollients known from the prior art and suitable for use on skin and hands. Of suitability here are in particular partial glycerides, i.e. monoglycerides, diglycerides and technical-grade mixtures thereof which, as a result of the production, may also contain small amounts of triglycerides. Typical examples are mono- and/or diglycerides based on caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, arachic acid, gadoleic acid, behenic acid and erucic acid, and also technical-grade mixtures thereof. Preference is given to using technical-grade lauric acid glycerides, palmitic acid glycerides, stearic acid glycerides, isostearic acid glycerides, oleic acid glycerides, behenic acid glycerides and/or erucic acid glycerides, which have a monoglyceride fraction in the range from 50 to 95, preferably 60 to 90% by weight. The preferred partial glycerides here are the oleic acid glycerides.

It may be very particularly advantageous if the emollients used are polyol esters and/or polyol partial esters. Preferred emollients are partial glycerides, in particular polyglycerol partial esters. According to the invention, the emollient preferably present in the composition is polyglycerol partial ester of the general formula (I)

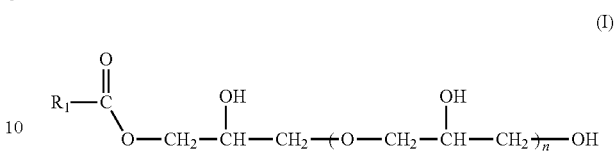

where
$R_1$=linear, branched or cyclic, saturated or unsaturated alkyl or alkenyl radical having 6 to 18, preferably 6 to 16 and preferably 8 to 12 carbon atoms and
n=integer from 1 to 9, preferably from 1 to 3, polyglycerol ether, polyglycerol ester and/or a polysaccharide derivative.

Furthermore, it is also possible to use polyglycerol esters with a different structure, e.g. on the basis of 1,2- or 1,3-linked polyglycerols.

If the compositions according to the invention have polyglycerol partial esters and/or polyglycerol fatty acid esters as emollients, then these can be selected e.g. from polyglcyerol-3 caprate and polyglycerol-4 caprate, which are available from Evonik Goldschmidt GmbH under the name TEGOSOFT® PC31 and TEGOSOFT® PC41.

If the compositions according to the invention have polyethylene glycol esters as emollients, then these are preferably PEG-7 glyceryl cocoate, which is available e.g. from Croda Chemicals Europe Ltd. under the name Glycerox HE.

If the compositions according to the invention have polysaccharide derivatives as emollients, then these may be in particular polysaccharide esters and/or polysaccharide ethers and/or polysaccharide glycosides. Preferred polysaccharide derivatives are e.g. sucrose and sorbitan esters, as can be acquired, for example, from Evonik Goldschmidt GmbH under the names TEGOSOFT® LSE 65 K Soft and ANTIL® Soft SC LSE 65 K Soft.

A further preferred emollient class is the lactates, as are sold, for example, by Sasol under the name Cosmal® ELI.

d) Surfactants

As surfactants, the compositions according to the invention can have all surfactants suitable for hand and skin cleansers. Suitable surfactants d) preferably include none of the compounds specified under c) as emollients.

Surfactants which may be present in the composition are anionic, nonionic, cationic and/or amphoteric surfactants. Typical examples of anionic surfactants are soaps, alkylbenzenesulphonates, alkanesulphonates, olefinsulphonates, alkyl ether sulphonates, glycerol ether sulphonates, alpha-methyl ester sulphonates, sulpho fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulphosuccinates, mono- and dialkyl sulphosuccinamates, sulphotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants contain polyglycol ether chains, these can have a conventional homolog distribution, but preferably have a narrowed homolog distribution. Typical examples of nonionic sulfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucoronic acid derivaties, fatty acid N-alkyl-glucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homolog distribution, but preferably have a narrowed homolog distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric and zwitterionic surfactants are alkylbetaines, alkylamidobetaines, aminopropionates, aminoglycinates, imidazoliniumbetaines and sulphobetaines. The specified surfactants are exclusively known compounds. As regards structure and preparation of these substances, reference may be made to relevant review works, for example J. Falbe (ed.), "Surfactants in Consumer Products", Springer Verlag, Berlin, 1987, pp. 54-124 or J. Falbe (ed.), "Katalysatoren, Tenside and Mineralöladditive [Catalysts, surfactants and mineral oil additives]", Thieme Verlag, Stuttgart, 1978, pp. 123-217. Typical examples of particularly suitable mild, i.e. particularly skin-compatible, surfactants are fatty alcohol polyglycol ether sulphates, monoglyceride sulphates, mono- and/or dialkyl sulphosuccinates, fatty acid isethionates, fatty acid sarcosinates, fatty acid taurides, fatty acid glutamates, alpha-olefin sulphonates, ether carboxylic acids, alkyl oligoglucosides, fatty acid glucamides, alkylamidobetaines, amphoacetals and/or protein fatty acid condensates, the latter preferably on the basis of wheat proteins.

The fraction of surfactants in the composition according to the invention is preferably 2 to 40% by weight, preferably 3 to 20 and particularly preferably 5 to 10% by weight, based on the total composition.

The surfactant present in the composition according to the invention is preferably at least one compound selected from the group of fatty alcohol ethoxylates, fatty alcohol ether sulphates and salts of sulphated and/or sulphonated fatty acids.

It may be advantageous if the composition according to the invention has one or more fatty alcohol ethoxylates or salts thereof. Preferred fatty alcohol ethoxylates preferably have the general formula (II)

$$R^3\text{—}O\text{—}(CH_2\text{—}CH_2\text{—}O)_n H \quad (II)$$

where $R^3$=saturated, unsaturated, branched or unbranched alkyl radical, preferably having 6 to 18, preferably having 10 to 16 and particularly preferably having 11 to 14 carbon atoms, n=integer from 1 to 11, preferably 3 to 6 and preferably 5 to 7.

In a preferred embodiment, the compositions according to the invention comprise 5 to 10% by weight, based on the total composition, of laureth-6 as fatty alcohol ethoxylate.

Preferred fatty alcohol ether sulphates are preferably those of the general formula (III)

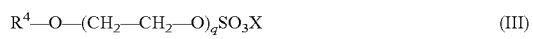

$$R^4\text{—}O\text{—}(CH_2\text{—}CH_2\text{—}O)_q SO_3 X \quad (III)$$

where $R^4$=a saturated or unsaturated, branched or unbranched hydrocarbon radical, preferably alkyl radical, having 8 to 18, preferably 11 to 14 carbon atoms, n=an integer from 1 to 6, preferably 1 to 4, and X=Na$^+$, NH$_4^+$ or Mg$^{2+}$, where sodium lauryl ether sulphate (where R=C$_{12}$, n=2-3 and X=Na$^+$) is particularly preferred.

If salts of sulphated and/or sulphonated fatty acids are present as surfactants in the composition according to the invention, then these are preferably ammonium, alkali metal or alkaline earth metal salts of $C_8$-$C_{30}$, preferably $C_{10}$-$C_{22}$ fatty acids, particularly preferably castor oil sulphates, in particular Na$^+$ or NH$_4^+$ sulphates. Such castor oil sulphonates are available for example under the names Monobrilliantöl® (Evonik Stockhausen GmbH, Krefeld) or Standapol SCO® (Henkel KGaA, Düsseldorf).

The surfactants used are particularly preferably mild surfactants or mild mixtures of surfactants, preferably selected from the surfactants specified above. Within the context of the present invention, mild surfactants are understood as meaning those which have an L/D quotient greater than 1. The L/D quotient represents the ratio of haemolysis value (L) to denaturing index (D) and is determined by the standard RBC test, as is described in WO03/028695 and the databases and documents cited therein. Preferred surfactants or mild mixtures of surfactants present in the composition according to the invention have an L/D value greater than or equal to 3, preferably greater than or equal to 5, preferably greater than 10, particularly preferably greater than 25 and very particularly preferably greater than 50.

Optional Constituents e) Abrasives

It may be advantageous if, as well as the superabsorbent particles, the composition according to the invention has one or more abrasives different from the superabsorbent particles. The fraction of additional abrasives can then be 0.05 to 15% by weight, preferably 0.1 to 10% by weight, particularly preferably 1 to 5% by weight, based on the total composition. Abrasives to be used with preference are, for example, synthetic abrasives based on polyethylene or polyurethane, abrasives based on natural kernel and/or shell flours, in particular walnut shell, almond shell, hazelnut shell, olive kernel, apricot kernel and cherry kernel flour or any desired mixtures of these shell and kernel flours and beads made of waxes, such as e.g. jojoba waxes, particular preference being given to hydrogen-peroxide-bleached or heat-treated natural kernel and/or shell flours, in particular walnut shell flour.

f) Viscosity Modifiers

To adjust the viscosity of the composition according to the invention, in particular to increase the viscosity, it may be advantageous if the composition according to the invention has one or more agents which are suitable for adjusting the viscosity, in particular for increasing the viscosity. Such agents can comprise, for example, organophilic and/or hydrophilic sheet silicates, in particular bentonites, polysaccharides, such as e.g. cellulose, guar flour and/or xanthans, modified polysaccharides, preferably cellulose ethers, carboxyalkylcellulose and/or hydroxyalkycelluloses, preferably hydroxyethylcellulose and/or inorganic electrolytes, preferably sodium chloride and/or magnesium sulphate. According to the invention, particularly preferred agents for increasing the viscosity of the composition according to the invention are carboxymethylcelluloses (e.g. Walocel CRT—Wolff Cellulosics, Walsrode), which, moreover, produce a foam-stabilizing effect upon application of the skin and hand cleansers according to the invention. The composition according to the invention preferably has 0.1 to 1.5% by weight, based on the total composition of viscosity modifiers.

g) Emulsifiers

It may be advantageous if the compositions according to the invention have emulsifiers. Preferably, the compositions according to the invention are free from emulsifiers.

h) Regulating Agents for the Swelling Behaviour of the Superabsorbent Particles

It may be advantageous if the compositions according to the invention and/or the superabsorbent particles have one or more regulating agents for the swelling behaviour. The fraction of regulating agent in the total composition is preferably from 1 to 10% by weight. Preferably, the compositions according to the invention and/or the superabsorbent particles have, as regulating agent, an inorganic salt, preferably a halogen salt of di- or trivalent cations, particularly preferably alkaline earth metal halides and very particularly preferably calcium chloride. As a result of the presence of regulating agents, the swelling of the superabsorbent particles in the aqueous formulations can be reduced. Too much swelling of the superabsorbent particles can lead to an increase in the viscosity of the composition according to the invention, meaning that the viscosity lies outside of the preferred range stated above, which is to be prevented.

i) Auxiliaries, Additives and/or Active Ingredients

As well as the aforementioned ingredients, the compositions according to the invention, in particular the skin and hand cleansers and particularly the heavy-duty hand cleansers, can comprise further cosmetic auxiliaries, additives and/or active ingredients, for example pH regulators, stabilizers, preferably cetearyl alcohol and/or hydrogenated castor oils, such as e.g. trihydroxystearin, fragrances, preservatives, preferably organic acids and antioxidants, such as e.g. vitamin E acetate. Preferably, oily or aqueous care components such as e.g. bisabolol, aloe vera, panthenol, sodium PCA, jojoba oil, creatine etc. may also be present in the composition according to the invention in order to emphasize the care effect. Stabilizers which may be present in the composition according to the invention are particularly preferably alkoxylated amides, such as e.g. PEG-4 rapeseed amide (Amidet N—Biesterfeld Spezialchemie GmbH, Hamburg).

If auxiliaries, additives and/or active ingredients are present in the composition according to the invention, the sum of the fractions of these substances is preferably from 0.5 to 5% by weight.

Preferred compositions according to the invention have, in each case based on the total composition of the composition:
- a.) 0.01 to 30% by weight, preferably 1 to 30% by weight, preferably from 1 to 10% by weight and particularly preferably from 2 to 8% by weight, of superabsorbent particles,
- b.) 10 to 90% by weight, preferably 30 to 80 and particularly preferably 45 to 75% by weight, of solvents, preferably water, preferably exclusively water,
- c.) 2 to 40% by weight, preferably 3 to 20 and particularly preferably 5 to 10% by weight, of at least one surfactant, preferably selected from the group of fatty alcohol ethoxylates, fatty alcohol ether sulphates and salts of sulphated and/or sulphonated fatty acids,
- d.) optionally one or more viscosity-forming and/or -modifying agents, emollients and/or abrasives,
- e.) optionally cosmetic auxiliaries, additives and/or active ingredients different from a) to d), where the sum of components a.) to e.) preferably gives 100% by weight. Preferably, the composition according to the invention consists of the aforementioned components.

The composition according to the invention is preferably a skin and hand cleanser, preferably a heavy-duty hand cleanser, or a surface cleaner or can be used as such.

The production of the compositions according to the invention, in particular skin and hand cleansers, preferably heavy-duty hand cleansers, or surface cleaners, can take place e.g. by means of known apparatuses in batch or continuous processes, the skin and hand cleansers preferably being obtained as creamy compositions or as flowable viscous pastes. Suitable apparatuses are heatable reactors with stirrer, continuous mixers such as extruders and dispersers.

The skin and hand cleansers according to the invention exhibit a very good cleaning effect, coupled with very good skin compatibility and low drying-out of the skin. It is particularly advantageous that the skin and hand cleansers according to the invention produce a very good skin feel during washing. Moreover, it could be observed that even with a slight oil contamination, the skin and hand cleansers according to the invention foam to a considerably greater extent than heavy-duty hand cleansers of the prior art. The skin feel after washing is significantly more pleasant, even after some time, on account of the lower drying-out of the skin.

The present invention is described by the examples below and with the help of the handwashing test, without being limited thereto.

Testing the Cleaning Power with the Help of the Handwashing Test

The test model of the handwashing test with standardized dirt or paint gives information about the cleaning effect of the products to be tested. It is required for practical relevance that all subjects have a characteristic skin structure on the palms of the hands caused by manual work. The following test is carried out in the morning and afternoon using one product in each case:

Test Procedure
- 0.5 g of model soiling are spread onto the palms of the hands and on the backs of the hands and rubbed in
- leave to dry for 2 min.
- 1.2 g of cleanser are applied and rubbed in
- 1 ml of water is added and washed for 30 s
- add a further 1 ml of water and leave to wash for 30 s
- rinse off under running cold water
- visual assessment of the residual soiling (RS) on the backs of the hand and the palms of the hand according to the scale see below 0=clean 5=no cleaning effect (grading in 0.5 steps possible)

The percentage cleaning effect is calculated in accordance with the following formula:

$$\text{Cleaning effect}[\%] = \frac{10 - (\overline{RS}_{palm} + \overline{RS}_{back})}{10} * 100\%$$

$\overline{RS}_{palm}$=average value of the residual soiling on the palms of the hand of n measurement series (subjects)

$\overline{RS}_{back}$=average value of the residual soiling on the backs of the hand of n measurement series (subjects)

Since the determination of the cleaning effect as a consequence of the test method has a greater spread, an absolute deviation of 5% between two measurement series is acceptable.

Composition of the Model Soiling (Soiling E) in % by Mass:

Engine oil: 54.15%
Vaseline: 18.05%
Wool wax: 18.05%
Graphite: 3.61%
Flame black: 5.42%
Iron oxide ($Fe_2O_3$): 0.72%

WORKING EXAMPLES

The following particles were used as superabsorbent particles:

SAP1: superabsorbent particles produced as preproduct B in US 2008/234420 A1, with a particle size of less than 150 μm SAP2: superabsorbent particles produced as Example 10 in US 2008/234420 A1, with a particle size of less than 150 μm SAP3: superabsorbent particles produced as powder A in DE 102006037983 A1, with a particle size of less than 150 μm SAP4: superabsorbent particles produced as powder A2 in DE 102006037983 A1, with a particle size of less than 150 μm SAP5: superabsorbent particles produced as powder C in DE 102006037983 A1, with a particle size of less than 150 μm SAP6: superabsorbent particles produced as powder C3 in DE 102006037983 A1, with a particle size of less than 150 μm SAP7: superabsorbent particles produced as powder A in DE 10125599 A1, with a particle size of less than 150 μm SAP8: superabsorbent particles from ADM available as Actyfill 20

SAP9: superabsorbent particles from Sumitomo, type SA60S

SAP4.1: as SAP4 with a particle size of from 100 to 200 μm
SAP4.2: as SAP4 with a particle size of from 200 to 300 μm
SAP4.3: as SAP4 with a particle size of from 300 to 400 μm
SAP4.4: as SAP4 with a particle size of from 400 to 500 μm
SAP4.5: as SAP4 with a particle size of from 500 to 600 μm
SAP4.6: as SAP4 with a particle size of from 600 to 700 μm
SAP4.7: as SAP4 with a particle size of >700 μm The respective particle fractions were obtained by sieving.

Skin and hand cleansers were produced according to the compositions given in Table 1 by stirring together all of the components using the cold-cold, hot-cold or hot-hot processes customary in cosmetics. The compositions were characterized with regard to their skin compatibility, skin drying-out and cleaning effect towards a model soiling and paint.

The formulations and results of the handwashing tests are summarized in Table 1.

TABLE 1

Formulations of the examples according to the invention in % by mass and results of the handwashing tests

| Ingredients according to INCI nomenclature | A | B | C | D | E | F | G | H | I |
|---|---|---|---|---|---|---|---|---|---|
| AQUA(WATER) | 75.25 | 75.25 | 75.25 | 75.25 | 75.25 | 75.25 | 75.25 | 75.25 | 75.25 |
| JUGLANS REGIA SHELL POWDER | 0 | 0 | 0 | 0 | 0 | 0 | 0 | 0 | 0 |
| LAURETH-6 | 6.0 | 6.0 | 6.0 | 6.0 | 6.0 | 6.0 | 6.0 | 6.0 | 6.0 |
| SODIUM LAURETH SULPHATE | 3.4 | 3.4 | 3.4 | 3.4 | 3.4 | 3.4 | 3.4 | 3.4 | 3.4 |
| SULPHATED CASTOR OIL | 2.7 | 2.7 | 2.7 | 2.7 | 2.7 | 2.7 | 2.7 | 2.7 | 2.7 |
| DISODIUM LAURETH SULPHOSUCCINATE | 1.8 | 1.8 | 1.8 | 1.8 | 1.8 | 1.8 | 1.8 | 1.8 | 1.8 |
| Sorbitan Sesquicaprylate (Antil soft SC) | 1.5 | 1.5 | 1.5 | 1.5 | 1.5 | 1.5 | 1.5 | 1.5 | 1.5 |
| POLYGLYCERYL-3 CAPRATE (Tegosoft PC 31) | 0 | 0 | 0 | 0 | 0 | 0 | 0 | 0 | 0 |
| SUCROSE COCOATE Tegosoft LSE-65Ksoft) | 0 | 0 | 0 | 0 | 0 | 0 | 0 | 0 | 0 |
| PPG-11 STEARYL ETHER (Varonic APS) | 0 | 0 | 0 | 0 | 0 | 0 | 0 | 0 | 0 |
| CARBOXYMETHYL CELLULOSE | 0.7 | 0.7 | 0.7 | 0.7 | 0.7 | 0.7 | 0.7 | 0.7 | 0.7 |
| XANTHAN GUM | 0.4 | 0.4 | 0.4 | 0.4 | 0.4 | 0.4 | 0.4 | 0.4 | 0.4 |
| SODIUM CHLORIDE | 1.5 | 1.5 | 1.5 | 1.5 | 1.5 | 1.5 | 1.5 | 1.5 | 1.5 |
| Oleic Acid | 1.2 | 1.2 | 1.2 | 1.2 | 1.2 | 1.2 | 1.2 | 1.2 | 1.2 |
| SODIUM BENZOATE | 0.6 | 0.6 | 0.6 | 0.6 | 0.6 | 0.6 | 0.6 | 0.6 | 0.6 |
| POTASSIUM SORBATE | 0.3 | 0.3 | 0.3 | 0.3 | 0.3 | 0.3 | 0.3 | 0.3 | 0.3 |
| PARFUM (FRAGRANCE) | 0.2 | 0.2 | 0.2 | 0.2 | 0.2 | 0.2 | 0.2 | 0.2 | 0.2 |
| CITRIC ACID | 0.45 | 0.45 | 0.45 | 0.45 | 0.45 | 0.45 | 0.45 | 0.45 | 0.45 |
| SAP1 | 4.0 | | | | | | | | |
| SAP2 | | 4.0 | | | | | | | |
| SAP3 | | | 4.0 | | | | | | |
| SAP4 | | | | 4.0 | | | | | |
| SAP5 | | | | | 4.0 | | | | |
| SAP6 | | | | | | 4.0 | | | |
| SAP7 | | | | | | | 4.0 | | |
| SAP8 | | | | | | | | 4.0 | |
| SAP9 | | | | | | | | | 4.0 |
| Handwashing test against soiling E | 1.1 | 1.1 | 0.8 | 0.8 | 1.3 | 1.1 | 1.4 | 1.8 | 1.8 |
| Viscosity [Pas] | >100 | >100 | >100 | >100 | >100 | >100 | >100 | >100 | >100 |

| Ingredients according to INCI nomenclature | J | K | L | M | N | O | P | Q | R |
|---|---|---|---|---|---|---|---|---|---|
| AQUA(WATER) | 75.25 | 75.25 | 75.25 | 75.25 | 75.25 | 75.25 | 75.25 | 75.25 | 75.25 |
| JUGLANS REGIA SHELL POWDER | 0 | 0 | 0 | 0 | 0 | 0 | 0 | 0 | 0 |
| LAURETH-6 | 6.0 | 6.0 | 6.0 | 6.0 | 6.0 | 6.0 | 6.0 | 6.0 | 6.0 |
| SODIUM LAURETH SULPHATE | 3.4 | 3.4 | 3.4 | 3.4 | 3.4 | 3.4 | 3.4 | 3.4 | 3.4 |
| SULPHATED CASTOR OIL | 2.7 | 2.7 | 2.7 | 2.7 | 2.7 | 2.7 | 2.7 | 2.7 | 2.7 |

TABLE 1-continued

Formulations of the examples according to the invention in % by mass and results of the handwashing tests

| Ingredient | | | | | | | | | |
|---|---|---|---|---|---|---|---|---|---|
| DISODIUM LAURETH SULPHOSUCCINATE | 1.8 | 1.8 | 1.8 | 1.8 | 1.8 | 1.8 | 1.8 | 1.8 | 1.8 |
| Sorbitan Sesquicaprylate (Antil soft SC) | 1.5 | 1.5 | 1.5 | 1.5 | 1.5 | 1.5 | 1.5 | 1.5 | 1.5 |
| POLYGLYCERYL-3 CAPRATE (Tegosoft PC 31) | 0 | 0 | 0 | 0 | 0 | 0 | 0 | 0 | 0 |
| SUCROSE COCOATE Tegosoft LSE-65Ksoft) | 0 | 0 | 0 | 0 | 0 | 0 | 0 | 0 | 0 |
| PPG-11 STEARYL ETHER (Varonic APS) | 0 | 0 | 0 | 0 | 0 | 0 | 0 | 0 | 0 |
| CARBOXYMETHYL CELLULOSE | 0.7 | 0.7 | 0.7 | 0.7 | 0.7 | 0.7 | 0.7 | 0.7 | 0.7 |
| XANTHAN GUM | 0.4 | 0.4 | 0.4 | 0.4 | 0.4 | 0.4 | 0.4 | 0.4 | 0.4 |
| SODIUM CHLORIDE | 1.5 | 1.5 | 1.5 | 1.5 | 1.5 | 1.5 | 1.5 | 1.5 | 1.5 |
| Oleic Acid | 1.2 | 1.2 | 1.2 | 1.2 | 1.2 | 1.2 | 1.2 | 1.2 | 1.2 |
| SODIUM BENZOATE | 0.6 | 0.6 | 0.6 | 0.6 | 0.6 | 0.6 | 0.6 | 0.6 | 0.6 |
| POTASSIUM SORBATE | 0.3 | 0.3 | 0.3 | 0.3 | 0.3 | 0.3 | 0.3 | 0.3 | 0.3 |
| PARFUM (FRAGRANCE) | 0.2 | 0.2 | 0.2 | 0.2 | 0.2 | 0.2 | 0.2 | 0.2 | 0.2 |
| CITRIC ACID | 0.45 | 0.45 | 0.45 | 0.45 | 0.45 | 0.45 | 0.45 | 0.45 | 0.45 |
| SAP4.1 | 4.0 | | | | | | | | |
| SAP4.2 | | 4.0 | | | | | | | |
| SAP4.3 | | | 4.0 | | | | | | |
| SAP4.4 | | | | 4.0 | | | | | |
| SAP4.5 | | | | | 4.0 | | | | |
| SAP4.6 | | | | | | 4.0 | | | |
| SAP4.7 | | | | | | | 4.0 | | |
| SAP4 | | | | | | | | 2.0 | |
| SAP4 | | | | | | | | | 6.0 |
| Handwashing test against soiling E | 1.2 | 1.5 | 1.5 | 1.4 | 1.5 | 1.7 | 0.9 | 1.7 | 0.8 |
| Viscosity [Pas] | >100 | >100 | >100 | >100 | >100 | >100 | >100 | >100 | >100 |

| Ingredients according to INCI nomenclature | S | T | U | V | W | X | Y | Z | ZA |
|---|---|---|---|---|---|---|---|---|---|
| AQUA(WATER) | 78.75 | 76.75 | 76.75 | 74.25 | 73.25 | 72.25 | 71.25 | 72.25 | 73.75 |
| JUGLANS REGIA SHELL POWDER | 0 | 0 | 0 | 0 | 0 | 0 | 0 | 0 | 0 |
| LAURETH-6 | 6.0 | 6.0 | 6.0 | 6.0 | 6.0 | 6.0 | 6.0 | 6.0 | 6.0 |
| SODIUM LAURETH SULPHATE | 2.6 | 2.6 | 2.6 | 3.4 | 3.4 | 3.4 | 3.4 | 3.4 | 3.4 |
| SULPHATED CASTOR OIL | 2.7 | 2.7 | 2.7 | 2.7 | 2.7 | 2.7 | 2.7 | 2.7 | 2.7 |
| DISODIUM LAURETH SULPHOSUCCINATE | 1.8 | 1.8 | 1.8 | 1.8 | 1.8 | 1.8 | 1.8 | 1.8 | 1.8 |
| Sorbitan Sesquicaprylate (Antil soft SC) | 1.5 | 1.5 | 1.5 | 1.5 | 1.5 | 1.5 | 1.5 | 0 | 0 |
| POLYGLYCERYL-3 CAPRATE (Tegosoft PC 31) | 0 | 0 | 0 | 0 | 0 | 0 | 0 | 0 | 0 |
| C12-13 ALKYL LACTATE (Cosmacol ELI) | 0 | 0 | 0 | 0 | 0 | 0 | 0 | 1.5 | 0 |
| PPG-11 STEARYL ETHER (Varonic APS) | 0 | 0 | 0 | 0 | 0 | 0 | 0 | 0 | 0 |
| CARBOXYMETHYL CELLULOSE | 0.7 | 0.7 | 0.7 | 0.7 | 0.7 | 0.7 | 0.7 | 0.7 | 0.7 |
| XANTHAN GUM | 0.4 | 0.4 | 0.4 | 0.4 | 0.4 | 0.4 | 0.4 | 0.4 | 0.4 |
| SODIUM CHLORIDE | 1.5 | 1.5 | 1.5 | 1.5 | 1.5 | 1.5 | 1.5 | 1.5 | 1.5 |
| Oleic Acid | 1.2 | 1.2 | 1.2 | 1.2 | 1.2 | 1.2 | 1.2 | 1.2 | 1.2 |
| PEG-4 RAPESEEDAMIDE | 1.0 | 1.0 | 1.0 | 0 | 0 | 0 | 0 | 0 | 0 |
| SODIUM BENZOATE | 0.6 | 0.6 | 0.6 | 0.6 | 0.6 | 0.6 | 0.6 | 0.6 | 0.6 |
| POTASSIUM SORBATE | 0.3 | 0.3 | 0.3 | 0.3 | 0.3 | 0.3 | 0.3 | 0.3 | 0.3 |
| PARFUM (FRAGRANCE) | 0.2 | 0.2 | 0.2 | 0.2 | 0.2 | 0.2 | 0.2 | 0.2 | 0.2 |
| CITRIC ACID | 0.45 | 0.45 | 0.45 | 0.45 | 0.45 | 0.45 | 0.45 | 0.45 | 0.45 |
| CALCIUM CHLORIDE | 0 | 0 | 0 | 1.0 | 2.0 | 3.0 | 4.0 | 3.0 | 2.0 |
| SAP5 | 0 | 2.0 | | | | | | | |
| SAP6 | | | 2.0 | 4.0 | 4.0 | 4.0 | 4.0 | 4.0 | 4.0 |
| Handwashing test against soiling E | 2.4 | 1.5 | 1.6 | 0.9 | 0.7 | 0.7 | 1.3 | 1.7 | 1.1 |
| Viscosity [Pas] | >100 | >100 | >100 | 70 | 30 | 25 | 16 | 26 | 28 |

| Ingredients according to INCI nomenclature | ZB | ZC | ZD |
|---|---|---|---|
| AQUA(WATER) | 70.6 | 65.6 | 69.6 |
| JUGLANS REGIA SHELL POWDER | 0 | 5.0 | 5.0 |
| LAURETH-6 | 6.0 | 6.0 | 6.0 |
| SODIUM LAURETH SULPHATE | 4.2 | 4.2 | 4.2 |
| SULPHATED CASTOR OIL | 1.8 | 1.8 | 1.8 |
| DISODIUM LAURETH SULPHOSUCCINATE | 2.7 | 2.7 | 2.7 |
| CARBOXYMETHYL CELLULOSE | 0.9 | 0.9 | 0.9 |
| XANTHAN GUM | 0.45 | 0.45 | 0.45 |
| SODIUM CHLORIDE | 2.0 | 2.0 | 2.0 |

TABLE 1-continued

Formulations of the examples according to the invention in % by mass and results of the handwashing tests

| Oleic Acid | 1.2 | 1.2 | 1.2 |
|---|---|---|---|
| PEG-4 RAPESEEDAMIDE | 3.0 | 3.0 | 3.0 |
| 2-BROMO-2-NITROPROPANE-1,3-DIOL (Bronopol) | 0.6 | 0.6 | 0.6 |
| PARFUM (FRAGRANCE) | 0.1 | 0.1 | 0.1 |
| CITRIC ACID | 0.45 | 0.45 | 0.45 |
| CALCIUM CHLORIDE | 2.0 | 2.0 | 2.0 |
| SAP6 | 4.0 | 4.0 | 0 |
| Handwashing test against soiling E | 2.1 | 1.1 | 3.5 |
| Viscosity [Pas] | 25 | 28 | 24 |

TABLE 2

Formulations of the comparative examples in % by mass and results of the handwashing tests

| Ingredients according to INCI nomenclature | SNF 1 | SNF 2 |
|---|---|---|
| AQUA (WATER) | 96.8 | 87.128 |
| SAP6 | 0.2 | 0.2 |
| OCTYL STEARATE (Tegosoft OS) | 0 | 10.0 |
| SODIUM POLYACRYLATE AND HYDROGEATED POLYDECENE TRIDECETH-6 (Rapithix A60) | 1.0 | 0.7 |
| PHENOXYETHANOL | 1.0 | 1.0 |
| PARFUM (FRAGRANCE) | 1.0 | 1.0 |
| Handwashing test against soiling E | 9.8 | 8.9 |

As can be seen in Table 1, the example formulations A to ZA according to the invention have a good cleaning in the described handwashing test, particularly when compared to the surfactant-free formulations described in DE 101 95 737 (Examples SNF 1 and 2), which are given in Table 2. Examples ZB to ZD show that superabsorber increases the washing power more than standard commercial abrasives, here walnut shell flour. If walnut shell flour and superabsorber are used, synergistic effects are obtained.

The invention claimed is:

1. A composition, comprising, based on a total weight of the composition:
   10% or more by weight of water;
   a surfactant;
   from 0.01 to 30% by weight of superabsorbent particles; and
   from 1 to 10% by weight of a regulating agent for swelling behaviour of the superabsorbent particles;
   wherein the regulating agent is an inorganic salt.

2. The composition according to claim 1, wherein a particle size of the superabsorbent particles is from 0.01 to 1 mm.

3. The composition according to claim 1, wherein the superabsorbent particles comprise a copolymer of at least acrylic acid and an alkali metal acrylate.

4. The composition according to claim 1, comprising:
   a) from 1 to 30% by weight of the superabsorbent particles,
   b) from 10 to 90% by weight of the water,
   c) from 2 to 40% by weight of the surfactant, and
   d) optionally at least one of a viscosity-forming agent, a viscosity-modifying agent, an emollient, and an abrasive, and
   e) optionally at least one of a cosmetic auxiliary, an additive, and an active ingredient different from a) to d), wherein
   a sum of components a) to e) is optionally 100% by weight, and
   the surfactant is selected from the group consisting of a fatty alcohol ethoxylate, a fatty alcohol ether sulphate and a salt of a sulphated fatty acid and a salt of a sulphonated fatty acid.

5. The composition according to claim 1, further comprising an emollient.

6. The composition according to claim 1, wherein a viscosity of the composition is from 10,000 to 80,000 mPas.

7. The composition according to claim 1, wherein the surfactant is at least one fatty alcohol ethoxylate of formula

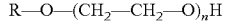

wherein
   R is a saturated, an unsaturated, a branched or an unbranched alkyl radical and
   n is an integer of from 1 to 11.

8. The composition according to claim 1 wherein the percent by weight of the superabsorbent particles is from 1 to 10.

9. The composition according to claim 1, wherein the superabsorbent particles comprise at least one of a polysaccharide, a natural raw material, and a renewable raw material.

10. The composition according to claim 1 wherein the water is the only solvent.

11. The composition according to claim 1, wherein the superabsorbent particles have not been subjected to a grinding process.

12. The composition according to claim 1, wherein the composition is a skin and hand cleanser or a surface cleaner.

13. A skin and hand cleanser or a surface cleaner, comprising the composition according to claim 1.

14. The composition according to claim 1, wherein the inorganic salt is calcium chloride.

* * * * *